US00PP14768P3

(12) United States Plant Patent
López

(10) Patent No.: US PP14,768 P3
(45) Date of Patent: May 11, 2004

(54) NECTARINE TREE NAMED 'PLATORNEC'

(50) Latin Name: *Prunus persica*
Varietal Denomination: Platornec

(75) Inventor: José Miguel Arias López, Tudela (ES)

(73) Assignee: Plantas de Navarra, S.A. (ES)

( * ) Notice: Subject to any disclaimer, the term of this patent is extended or adjusted under 35 U.S.C. 154(b) by 53 days.

(21) Appl. No.: 10/185,674

(22) Filed: Jun. 27, 2002

(65) Prior Publication Data

US 2004/0003441 P1 Jan. 1, 2004

(30) Foreign Application Priority Data

Oct. 23, 2001 (EP) ..... 2001/1669

(51) Int. Cl.[7] ..... A01H 5/00

(52) U.S. Cl. ..... Plt./190

(58) Field of Search ..... Plt./190

*Primary Examiner*—Bruce R. Campell
*Assistant Examiner*—Susan B. McCormick
(74) *Attorney, Agent, or Firm*—Christie, Parker & Hale, LLP

(57) ABSTRACT

A new and distinct variety of Nectarine Tree characterized by its low chilling requirement, producing a mid-season ripening, good quality, yellow fleshed, high firm, attractively colored and shaped fruit.

3 Drawing Sheets

Classification: The present invention relates to a new *Prunus persica* (L.) Batsch—Nectarine.

Variety denomination: The new plant has the varietal denomination 'Platornec'.

BACKGROUND OF THE INVENTION

The new variety of Nectarine tree was created in a breeding program by crossing two parents; in particular, by crossing as seed parent a variety designated '88-011' (unpatented) and as pollen parent a variety designated '88-052' (unpatented). Both, female and male, are components of a parent collection from a selection made between plants issued from seeds got in a free pollination in a population of different origin done in 1988. Both parental varieties are property and have not been commercialized.

The seeds resulting from this controlled hybridization were germinated in a greenhouse in the spring of 1997 and planted in a field on the farm of La Mogalla in Cartaya (Huelva), Spain, 7°W., 37°N., 45 feet elevation. The seedlings fruited during the spring of 1999 and one designated '97.14.012-N' (unpatented) was selected for its low chilling requirement (200 to 300 hours), its mid-season ripening, large, attractive fruit shape and color, yellow fleshed, good quality, medium-high firm fruit. During 1999, the original plant selection was propagated asexually, at the above noted location, by budding onto standard Peach rootstock variety designated 'GF-677' (non patented) and a test plot of 4 plants was established.

The new variety has been asexually multiplied several times since 1999 at this location by budding onto the standard Peach rootstock variety designated 'GF-677' (unpatented) and no incompatibility with Peach rootstock has occurred following budding. During all asexual reproduction, the characteristics of the original plant have been maintained and no aberrant phenotypes have appeared.

SUMMARY OF THE INVENTION

The new variety of Nectarine tree differs from its parents and other known cultivars of Nectarine trees by producing clingstone fruits with a low chilling requirement (200 to 300 hours) and very mid-season ripening date. The fruits of the new variety are ripe for commercial harvesting and shipment between approximately June 2$^{nd}$ to June 15$^{th}$. These harvesting dates are approximately 30 days earlier than the harvest dates of the commercial Nectarine variety 'Flameglo' (U.S. Plant Pat. No. 8,441), approximately 20 to 25 days later than the harvest dates of the commercial Nectarine variety 'Mayglo' (U.S. Plant Pat. No. 5,245) and approximately 28 days later than the harvest dates of the commercial Nectarine variety 'Earliglo' (U.S. Plant Pat. No. 7,402).

COMPARISON WITH OTHER VARIETIES

'Platornec' produces large, round shaped fruit with the apex depressed, showing the flesh fine and light colored fibers; whereas the fruit apex of 'Earliglo,' is level with no showing of flesh fibers. 'Platornec' produces higher quality flowers, more brilliant fruit and has a lower tendency stone to split than 'Earliglo.'

The fruit surface of 'Platornec' is covered almost 100% in a dark red color; whereas the fruit surface of 'Mayglo' is covered approximately 75% to 85% and its skin ground color is yellow. The fruit of the new variety has a low skin cracking susceptibility.

'Platornec' has a lower chilling requirement (200 to 300 hours) than the chilling requirement of 'Flameglo' (900 to 1000 hours).

BRIEF DESCRIPTION OF THE DRAWINGS

The accompanying photographic illustrations show typical specimens of the new variety in color as nearly true as is reasonably possible to make in illustrations of this character.

DESCRIPTION OF THE NEW VARIETY

Figure 1:
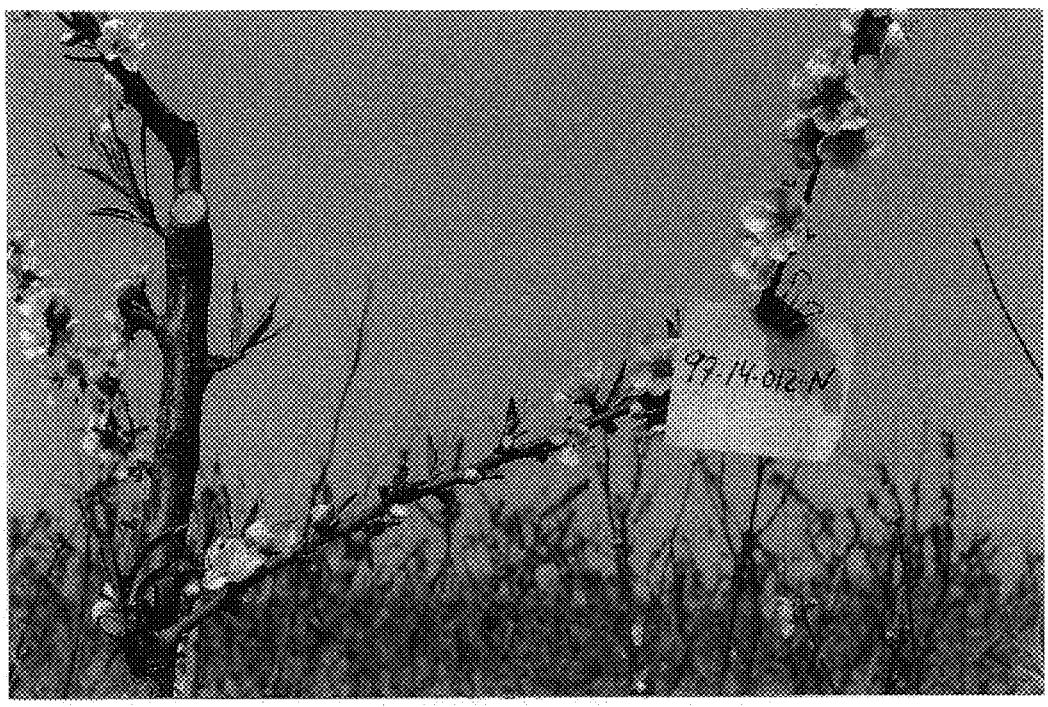
FIG. 1 shows typical flowers of the new variety.
Figure 2:
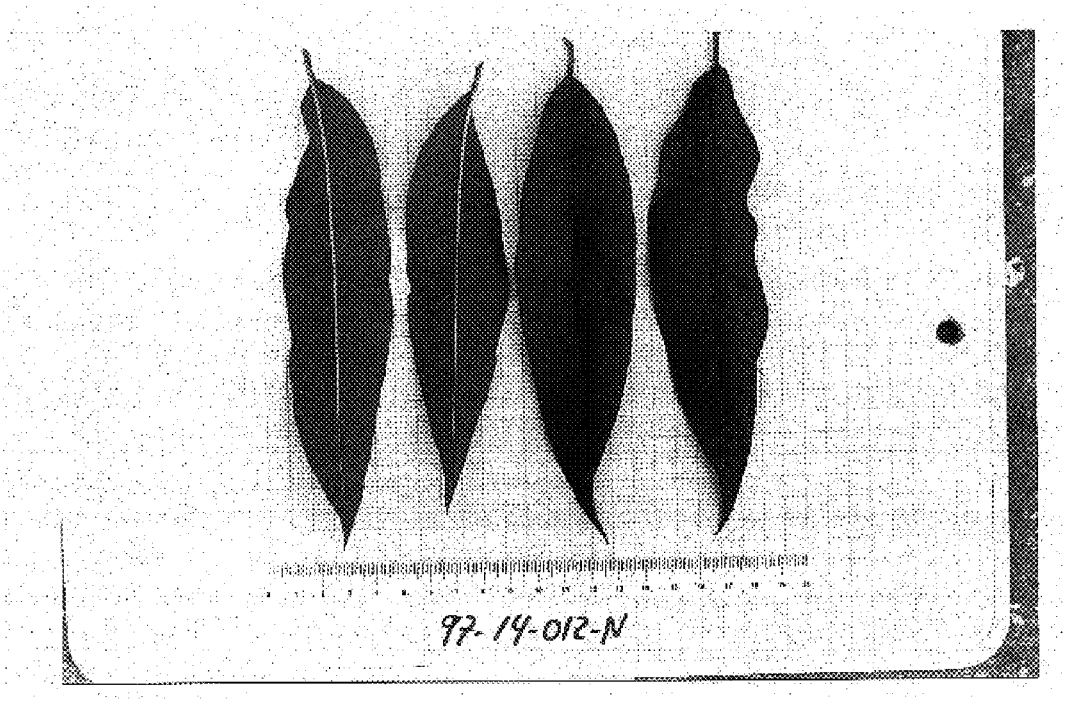
FIG. 2 shows the coloration of the dorsal and ventral leaves of the new variety.
Figure 3:
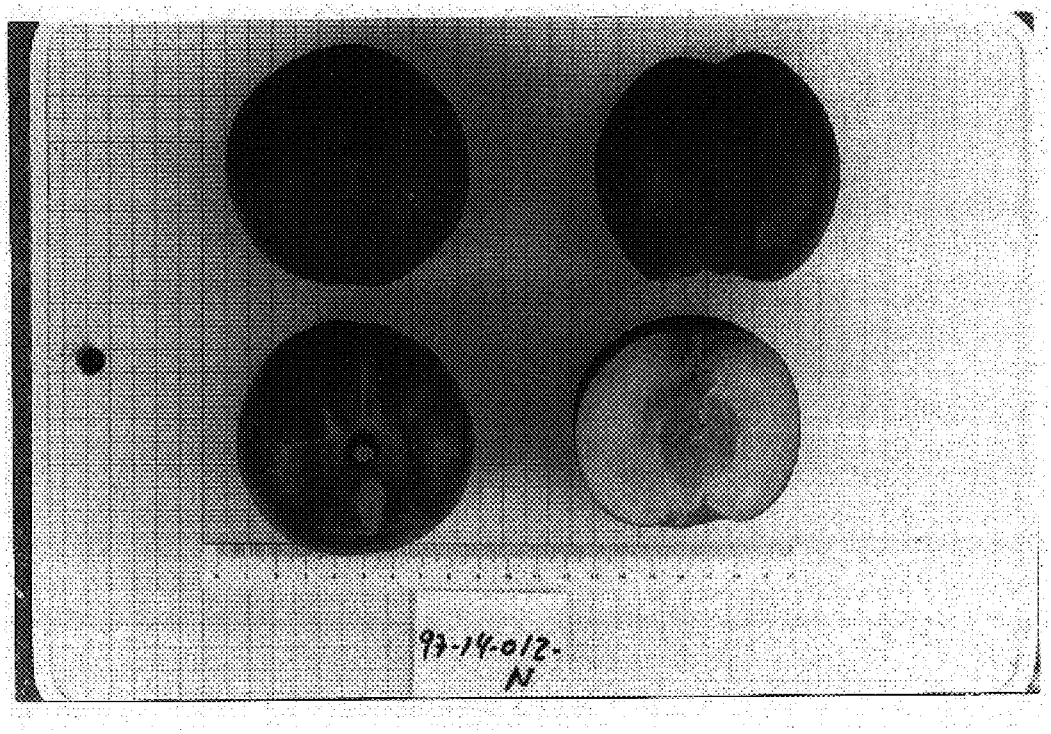
FIG. 3 shows the external coloration of fruits of the new variety when sufficiently matured for harvesting and shipment and one fruit of the new variety dissected in the equatorial plane to illustrate the flesh and stone characteristics.

The following observations and descriptions are of plants grown at the orchard previously described, located near the town of Cartaya, Huelva, Spain. Observations were made of the original seedling tree on its own root during the growing years of 1999 to 2001. The plants described are from seed germinated in the Spring of 1997, planted in December 1997. First fruit was observed in the Spring of 1999.

In this description, it is to be understood that references of the dimensions, sizes, colors, etc. of the botanical and phonological characteristics of the new variety are approximations of averages set forth as accurately as practical. Phenotypic expression may vary with light intensity and cultural and environmental conditions. The color references used in this description, are to The Royal Horticultural Society Colour Chart (R.H.S.C.C.) and terminology used in the color descriptions herein refers to plate numbers in said color chart.

Tree:

*Size.*—Average to above-average as compared to other common Nectarine cultivars.

*Productivity.*—Approximately 25000 to 28000 Kgrs/Ha.

*Form.*—Considered upright to upright, spreading in form.

*Height.*—Original seedling tree reached approximately 3.35 m at end of 2001 growing season.

*Width.*—Original seedling reached approximately 1.80 m at end of 2001 growing season.

*Current season growth.*—Approximately 0.90 to 1.10 m.

*Regularity of bearing.*—Regular.

Trunk:

*Thickness.*—Approximately 115 mm.

*Diameter.*—Approximately 15 cm when measured at a distance above the soil level at end of 2001 growing season.

*Bark texture.*—Considered moderately rough with numerous scarf skin and flat oval lenticels present.

*Bark coloration.*—Grey Group near 201D.

Branches:

*Size.*—Considered medium for the species. Diameter: About 65.2 mm when measured during $3^{rd}$ year after grafting.

*Surface texture.*—Average. Current Season Shoots: Substantially glabrous. Color: Greyed-green group near 194D to 194C. Mature Branches: Appearing furrowed on several year old wood. Color: Greyed-green Group near 197C to 201D.

Leaf:

*Size.*—Considered average for the species; leaf measurements taken from vigorous upright current season growth at approximately midshoot. Length: Approximately 150 to 186 mm. Width: Approximately 40 to 52 mm. Thickness: Approximately 1 to 2 mm.

*Base shape.*—Slightly oblique.

*Form.*—Lanceolate.

*Tip form.*—Acuminate.

*Color.*—Upper Side: Yellow-green Group near 146A to 147A. Underside: Yellow-Green Group near 147C to 147B.

*Texture.*—Glabrous.

*Margins.*—Crenate, generally uniform.

*Leaf petiole.*—Considered medium. Length: Approximately 8 to 13 mm. Diameter: Approximately 1.5 to 2 mm.

*Leaf glands.*—Reniform; generally 2 to 4 per side. Length: Approximately 1.5 to 2 mm. Width: Approximately 1.0 to 1.5 mm.

*Sepals.*—Length about 8 mm, width about 5 mm, usually 5 per flower, color near 178A to 181A.

*Venation.*—Pinnately net veined, mid-vein color between 149D to 150D.

Inflorescence:

*Flower bud.*—Length about 7 mm, diameter about 2 mm; shape ovoid; color between 177B to 177A.

*Flowers.*—Bloom occurs prior to vegetative bud break; generally 2 individual flowers at a single node; perfect self-fertile. Blooming Time: Considered early in relation to other Nectarine cultivars. Date of Bloom: First, February $7^{th}$ Full, February $14^{th}$. Flower Diameter: Approximately 40 to 46 mm at full bloom. Bloom Quantity: Considered very abundant. Petalage: Generally considered medium for the species. Length: Approximately 15 to 19 mm. Width: Approximately 12 to 15 mm. Shape: Lengthened. Petal Count: Nearly always 5. Texture: Glabrous. Color: Near 62D to 65D; abaxial color of petal near 69D to 69C. Apex: Petal apices appear domed. Flower Pedicel: Length about 3 mm, diameter about 2 mm, color near 144C. Stamens: Numerous with pollen present; fertile and abundant.

Reproductive organs:

*Anthers.*—Length about 1.5 to 1.7 mm, width about 1 mm; color between 187C to 188D.

*Pollen production.*—Pollen is abundant, color between 20B to 19A.

*Filaments.*—Length about 16 mm, color between 63D to 63C, darkening with advanced maturity.

*Pistil.*—Length about 16 mm, including ovary, surface texture glabrous, color near 150C.

Fruit: In firm ripe condition at full commercial maturity, first fruit picked on approximately June $2^{nd}$; last pick of same fruit in 2001 was approximately June $15^{th}$ in Cartaya, Huelva, Spain conditions.

*Size.*—Uniform, medium in size. Cheek Diameter: Average about 82 to 84 mm. Suture Diameter: Average about 80 to 82 mm. Axial diameter: Average about 75 to 77 mm.

*Form.*—Rounded, generally uniform.

*Suture.*—Extending from base to apex, suture appears as a very thin line at same level as skin.

*Stem cavity size.*—Considered medium for the species. Width: Approximately 25 to 30 mm. Length: Approximately 30 to 35 mm. Depth: Approximately 16 to 18 mm. Form: Rounded.

*Fruit base.*—Rounded; slightly concave in form; uniform.

*Fruit apex.*—Generally considered depressed.

*Fruit skin.*—Average in thickness. Surface Texture: Very glabrous. Skin Acidity: Neutral.

*Tenacious to flesh.*—Yes; at commercial maturity.

*Tendency to crack.*—Not observed. Skin Color: Approximately 100% of fruit surface covered with very brilliant Red-purple Group near 60A to 59A.

*Firmness.*—4.5 $Kg/cm^2$=Resistance to penetration measured in Kilograms ($Kg/cm^2$) obtained by Penetrometer ROZE Mod. Arbelette, with a 50 $mm^2$ section head.

*Flesh color.*—Yellow Group near 11B to 11A. Flesh Fibers: Fine, light red colored fibers present throughout flesh at maturity; overall at apex. Flesh Texture: Generally melting.

*Flavor.*—Considered sweet; medium acidic; soluble solids, as °Brix −12.

*Aroma.*—Pleasant and medium.

*Eating quality.*—Very good to excellent; well above average when compared to other common commercial varieties.

*Stone.*—Attachment: Clingstone at full commercial maturity. Stone Size: Considered medium for species. Length: Approximately 25 to 30 mm. Width: Approximately 25 to 30 mm. Thickness: Approximately 20 to 25 mm. Stone Form: Generally rounded. Stone Color: Yellow-Orange Group near 18A to 19A.

*Tendency to split.*—None observed.

*Kernel.*—Rounded in form. Length: Approximately 18 to 20 mm. Width: Approximately 18 to 20 mm.

General: Considered mid-season maturing Nectarine with a low chilling requirement (200 to 300 hours), large, attractively shaped, high firm fruit with brilliant dark red skin and yellow flesh.

Keeping quality: Fruit stored well up to 20 to 25 days after harvest at temperatures of about 1° C.

Resistance to insects and disease: No particular susceptibilities were noted.

Shipping quality: Well above average.

Hardiness: No Winter injury has been noted during years of evaluation in the South of Spain, drought and heat tolerance not noted.

The characteristics described above are as a result of as a result of the growing conditions prevailing in Cartaya, Huelva, Spain. It should be expected that variations in these characteristics may occur when farmed in areas with different climatic conditions, different soil types, and/or varying cultural practices.

I claim:

1. A new and distinct variety of Nectarine Tree substantially as illustrated and described herein.

* * * * *